US010241083B2

United States Patent
Schulz

(10) Patent No.: US 10,241,083 B2
(45) Date of Patent: Mar. 26, 2019

(54) ULTRASONIC INSPECTION PROBE ASSEMBLY

(71) Applicant: General Electric Company, Schenectady, NY (US)

(72) Inventor: Matthias Christoph Schulz, Duisburg (DE)

(73) Assignee: General Electric Company, Schenectady, NY (US)

( * ) Notice: Subject to any disclaimer, the term of this patent is extended or adjusted under 35 U.S.C. 154(b) by 115 days.

(21) Appl. No.: 15/068,169

(22) Filed: Mar. 11, 2016

(65) Prior Publication Data

US 2017/0261472 A1    Sep. 14, 2017

(51) Int. Cl.
| | |
|---|---|
| *G01N 29/04* | (2006.01) |
| *G01N 29/24* | (2006.01) |
| *B06B 1/06* | (2006.01) |
| *G01N 29/22* | (2006.01) |
| *G01N 29/26* | (2006.01) |
| *G01N 29/28* | (2006.01) |
| *G10K 11/32* | (2006.01) |

(52) U.S. Cl.
CPC ......... *G01N 29/041* (2013.01); *B06B 1/0622* (2013.01); *B06B 1/0696* (2013.01); *G01N 29/223* (2013.01); *G01N 29/24* (2013.01); *G01N 29/245* (2013.01); *G01N 29/262* (2013.01); *G01N 29/28* (2013.01); *G10K 11/32* (2013.01); *G01N 2291/106* (2013.01); *G01N 2291/2638* (2013.01)

(58) Field of Classification Search
CPC .... G01N 29/041; G01N 29/223; G01N 29/24; G01N 29/245; G01N 29/262; G01N 29/28

USPC .......................................................... 73/632
See application file for complete search history.

(56) References Cited

U.S. PATENT DOCUMENTS

| | | | |
|---|---|---|---|
| 4,628,573 A | 12/1986 | Hamada et al. | |
| 5,680,863 A * | 10/1997 | Hossack | A61B 8/12 600/437 |
| 7,878,977 B2 | 2/2011 | Mo et al. | |
| 8,270,254 B2 | 9/2012 | Casula | |
| 8,649,185 B2 | 2/2014 | Wodnicki et al. | |
| 2004/0249285 A1 | 12/2004 | Deng et al. | |
| 2008/0098816 A1* | 5/2008 | Yamashita | B06B 1/0629 73/596 |
| 2010/0171395 A1* | 7/2010 | Cannata | H01L 41/047 310/366 |
| 2011/0178583 A1* | 7/2011 | Gerlitz | A61N 5/0616 607/89 |

(Continued)

OTHER PUBLICATIONS

"WrapIT Flexible Phased Array Scanning tool," Retrieved from Internet URL: https://web.archive.org/web/20140531090950/http://www.phoenixisl.com/wrapit, pp. 2 (Jan. 4, 2018).

(Continued)

*Primary Examiner* — Son T Le
*Assistant Examiner* — Tarun Sinha
(74) *Attorney, Agent, or Firm* — Mintz Levin Cohn Ferris Glovsky and Popeo, P.C.

(57) ABSTRACT

An ultrasonic inspection probe assembly includes a flexible ultrasonic transducer array located between a backing block and a face layer. The flexible ultrasonic transducer array can be located in the opening of a flexible ultrasonic transducer array frame.

18 Claims, 3 Drawing Sheets

(56) References Cited

U.S. PATENT DOCUMENTS

| | | |
|---|---|---|
| 2013/0233082 A1 | 9/2013 | Bond-Thorley et al. |
| 2014/0137650 A1 | 5/2014 | Kleinert et al. |
| 2015/0078136 A1* | 3/2015 | Sun .................. G01N 29/223 367/180 |
| 2015/0219602 A1 | 8/2015 | Bond-Thorley et al. |
| 2016/0231289 A1* | 8/2016 | Laudermilch ......... B06B 1/0622 |

OTHER PUBLICATIONS

Extended European Search Report and Opinion issued in connection with corresponding EP Application No. 17160112.3 dated Jul. 25, 2017.

\* cited by examiner

ULTRASONIC INSPECTION PROBE ASSEMBLY

BACKGROUND

The subject matter disclosed herein relates to ultrasonic inspection systems and, more specifically, to an ultrasonic inspection probe assembly.

Ultrasonic inspection probes can be used by an inspection technician to inspect a test object by placing the probe on the surface of the test object and maneuvering the probe along the surface. In some cases, the test object has a curved or contoured surface where the contour changes along the surface of the test object. Some examples of these curved surfaces to be inspected include the bond seams of doors and hoods of cars that require inspection to ensure adequate bonding. Some ultrasonic inspection probes are spring loaded or use hydraulics or pneumatics to create the necessary force to adapt a flexible ultrasonic probe assembly to the curved surface. These existing flexible ultrasonic probe designs are complex and do not retain their original shape after being applied to the curved surface.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the disclosed subject matter encompasses other embodiments as well. The drawings are not necessarily to scale, emphasis generally being placed upon illustrating the features of certain embodiments of the invention. In the drawings, like numerals are used to indicate like parts throughout the various views.

SUMMARY

An ultrasonic inspection probe assembly includes a flexible ultrasonic transducer array located between a backing block and a face layer. The flexible ultrasonic transducer array can be located in the opening of a flexible ultrasonic transducer array frame. An advantage that may be realized in the practice of some disclosed embodiments of the ultrasonic inspection probe assembly is that the flexible assembly can be adapted to fit the shape of curved or contoured surfaces during inspection and then retain its original shape after inspection.

In one embodiment, an ultrasonic inspection probe assembly is disclosed. The ultrasonic inspection probe assembly comprises a backing block, a face layer, a flexible ultrasonic transducer array located between the backing block and the face layer, and a flexible ultrasonic transducer array frame located between the backing block and the face layer, the flexible transducer array frame comprising an opening, wherein the opening of the flexible ultrasonic transducer array frame surrounds the flexible ultrasonic transducer array.

In another embodiment, the ultrasonic inspection probe assembly comprises a backing block, a face layer, a flexible ultrasonic transducer array formed from a piezo-ceramic material and located between the backing block and the face layer, and a flexible ultrasonic transducer array frame located between the backing block and the face layer, the flexible transducer array frame comprising an opening, wherein the opening of the flexible ultrasonic transducer array frame surrounds the flexible ultrasonic transducer array, and wherein the flexible ultrasonic transducer array and the flexible ultrasonic transducer are bonded to the backing block and the face layer with an epoxy to form an acoustic stack.

The above embodiments are exemplary only. Other embodiments are within the scope of the disclosed subject matter.

DETAILED DESCRIPTION

Embodiments of the disclosed subject matter provide an ultrasonic inspection probe assembly that includes a flexible ultrasonic transducer array located between a backing block and a face layer. The flexible ultrasonic transducer array can be located in the opening of a flexible ultrasonic transducer array frame. Other embodiments are within the scope of the disclosed subject matter.

Figure 1:
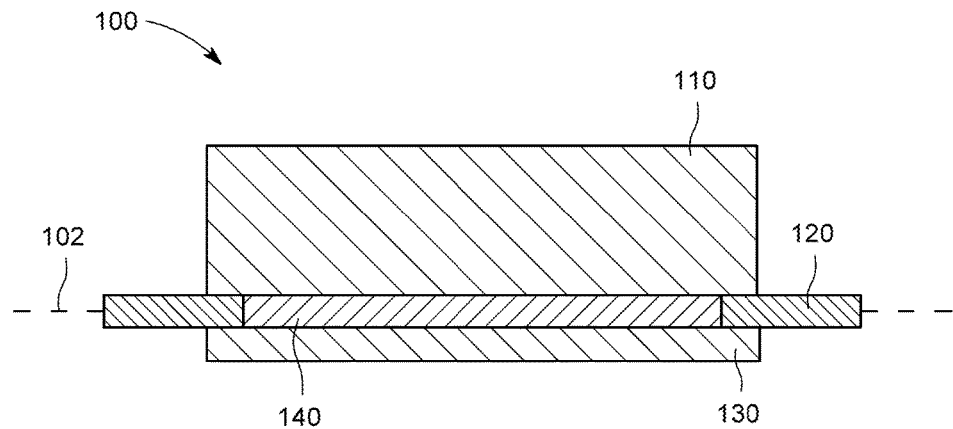
FIG. 1 is a section view of an exemplary ultrasonic inspection probe assembly.
Figure 2:
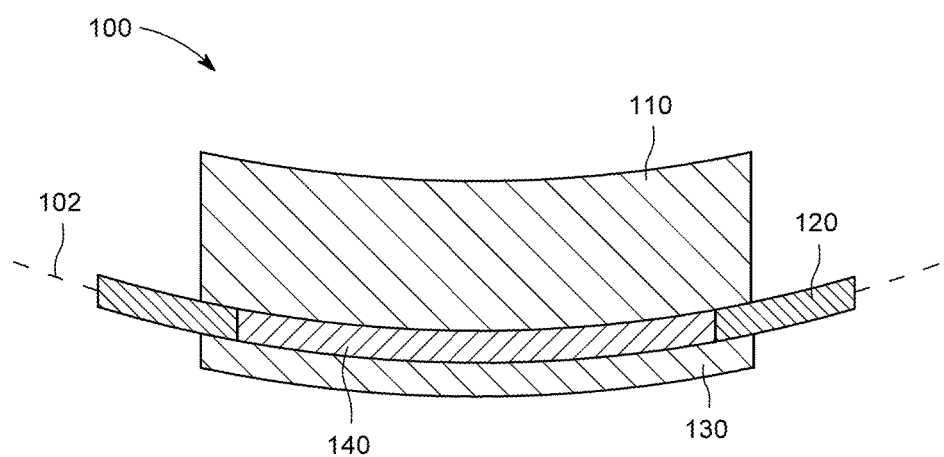
FIG. 2 is a section view of the exemplary ultrasonic inspection probe assembly of FIG. 1 shown in a flexed position.
Figure 3:
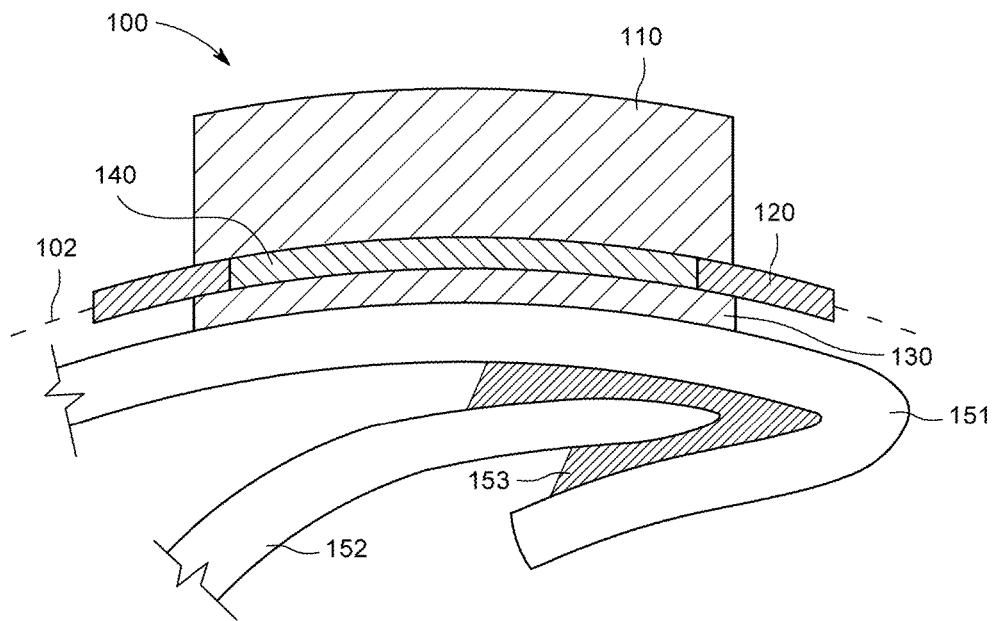
FIG. 3 is a section view of the exemplary ultrasonic inspection probe assembly of FIG. 1 applied to a test object.

FIG. 1 is a section view of an exemplary ultrasonic inspection probe assembly 100. FIG. 2 is a section view of the exemplary ultrasonic inspection probe assembly 100 of FIG. 1 shown in a flexed position. FIG. 3 is a section view of the exemplary ultrasonic inspection probe assembly 100 of FIG. 1 applied to a test object. It will be understood that the section view of the ultrasonic inspection probe assembly 100 of FIGS. 1-3 shows the acoustic stack of the ultrasonic inspection probe assembly 100. In one embodiment, the ultrasonic inspection probe assembly 100 includes a flexible ultrasonic transducer array 140 located between a backing block 110 and a face layer 130. In one embodiment, the backing block 110, the flexible ultrasonic transducer array frame 120, the flexible ultrasonic transducer array 140, and the face layer 130 can be bonded together using an adhesive material (e.g., epoxy). It will be understood that the acoustic stack of the ultrasonic inspection probe assembly 100 can have additional elements or elements configured in a different manner.

The backing block 110 supports the flexible ultrasonic transducer array 140 and can assist in damping the vibrations created by the flexible ultrasonic transducer array 140. In one embodiment, the backing block 110 can be made from a two component rubber that allows the backing block 110 to flex. The backing block 110 can be made of a nonconductive material with an impedance similar to the flexible ultrasonic transducer array 140. The damping effect allows the flexible ultrasonic transducer array 140 to have a higher sensitivity and produce more accurate results.

In one embodiment of the exemplary ultrasonic inspection probe assembly 100, the face layer 130 can be a thin layer of epoxy (e.g., EPDXIBOND EB-108). In one embodiment, the thickness of the face layer 130 can be 0.1 mm.

In the exemplary ultrasonic inspection probe assembly 100, the flexible ultrasonic transducer array 140 can be a linear phased array or a matrix phased array with a plurality of ultrasonic transducers formed from a piezo-ceramic material. In one embodiment, the flexible ultrasonic transducer array 140 can be formed from a monolithic ceramic that is kerfed, with the kerfs filled with epoxy to create the array of ultrasonic transducers, where each transducer is formed from a plurality of ceramic pillars extending between the kerfs. In one embodiment, the flexible ultrasonic transducer array 140 can have a pitch in the range of 0.5 to 1.0 mm and have 32 to 64 ultrasonic transducers. The thickness of the flexible ultrasonic transducer array 140 can vary depending upon the desired frequency. For example, for a 10 MHz probe, the flexible ultrasonic transducer array 140 can have a thickness of 0.1 mm, while a 5 MHz probe will have a thicker flexible ultrasonic transducer array 140 and a 15 MHz probe will have a thinner flexible ultrasonic transducer array 140.

Figure 4:
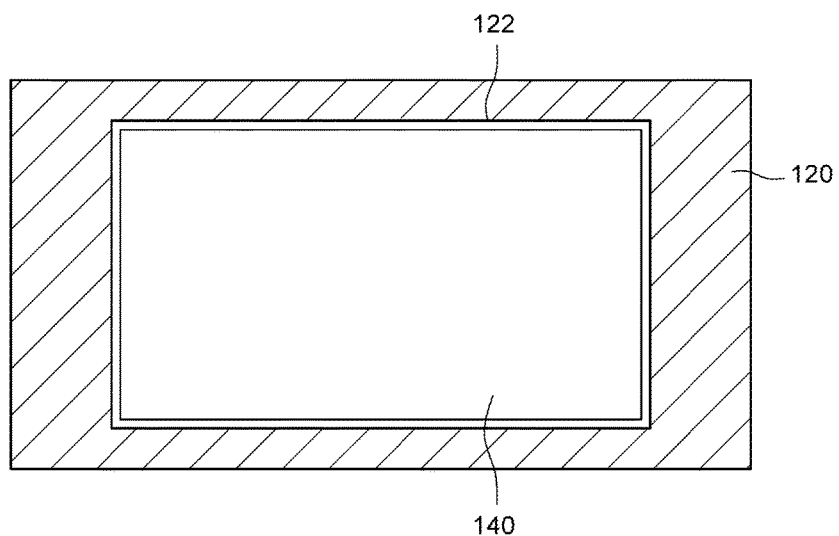
FIG. 4 is a top view of an exemplary flexible ultrasonic transducer array located in the opening of a flexible ultrasonic transducer array frame.

As shown in FIG. 4, the flexible ultrasonic transducer array 140 can be located in the opening 122 (or cutout) of a flexible ultrasonic transducer array frame 120, which can also located between the backing block 110 and the face layer 130. As will be explained, the flexible ultrasonic transducer array 140 can be located in the neutral phase 102 of the acoustic stack of the ultrasonic inspection probe assembly 100 formed by the flexible ultrasonic transducer array frame 120 to minimize the forces experienced by the flexible ultrasonic transducer array 140 when the ultrasonic inspection probe assembly 100 is flexed when applied to a curved test object.

As shown in FIG. 4, in one embodiment, the flexible ultrasonic transducer array frame 120 has an opening 122 surrounding the flexible ultrasonic transducer array 140. The size of the opening 122 can be equal to or slightly greater than (e.g., the width of one of the transducer elements) the size of the flexible ultrasonic transducer array 140 to allow for secure placement of the flexible ultrasonic transducer array 140 within the flexible ultrasonic transducer array frame 120. As shown in FIGS. 1-3, the thickness of the flexible ultrasonic transducer array 140 can be the same thickness as the flexible ultrasonic transducer array frame 120. In another embodiment, the flexible ultrasonic transducer array 140 can be a different thickness than the flexible ultrasonic transducer array frame 120. The flexible ultrasonic transducer array frame 120 allows the flexible ultrasonic inspection probe assembly 100 to flex or deflect from its original position during inspection of a curved object and then return to its original position afterwards, maintaining its original shape. In one embodiment, the flexible ultrasonic transducer array frame 120 can be made from spring steel (e.g., stainless steel 1.4310).

As shown in FIGS. 1-3, in one embodiment of the ultrasonic inspection probe assembly 100, the backing block 110 covers at least the width of the opening 122 of the flexible ultrasonic transducer array frame 120 to provide proper damping for the flexible ultrasonic transducer array 140. The face layer 130 can also cover at least the width of the flexible ultrasonic transducer array 140 to provide proper protection of the flexible ultrasonic transducer array 140.

As shown in FIG. 2, in one embodiment, the flexible ultrasonic transducer array frame 120 can be provided in a flexed (or bent) shape in its resting or original position when no forces are applied to the ultrasonic inspection probe assembly 100. The use of a flexed flexible ultrasonic transducer array frame 120 provides the benefit of a counter-force when the ultrasonic inspection probe assembly 100 is applied to a curved surface as shown in FIG. 3. In addition, the use of a flexed flexible ultrasonic transducer array frame 120 allows the flexible ultrasonic transducer array frame 120 and the rest of the ultrasonic inspection probe assembly 100 to return to its original shape and position once the ultrasonic inspection probe assembly 100 is removed from the surface of the test object.

As shown in FIG. 3, when the ultrasonic inspection probe assembly 100 is applied to a curved surface (e.g., the first plate 151 of an automotive part that is bonded to a second plate 152 using a bond seam 153), the components of the acoustic stack of the ultrasonic inspection probe assembly 100 (e.g., the face layer 130, the backing block 110, the flexible ultrasonic transducer array frame 120, and the flexible ultrasonic transducer array 140) all flex to adapt to the curve of the surface of the first plate 151. Since the flexible ultrasonic transducer array 140 is located in the neutral phase 102 of the acoustic stack of the ultrasonic inspection probe assembly 100 formed by the flexible ultrasonic transducer array frame 120, the flexible ultrasonic transducer array 140 is subjected to only minimal forces when the ultrasonic inspection probe assembly 100 is flexed onto the curved surface. This advantageously minimizes stress or forces experienced by the flexible ultrasonic transducer array 140. For example, as shown in FIG. 3, the backing block 110 will experience greater stretching or pulling apart than the flexible ultrasonic transducer array 140, while the face plate 130 will experience greater compression than the flexible ultrasonic transducer array 140.

Figure 5:
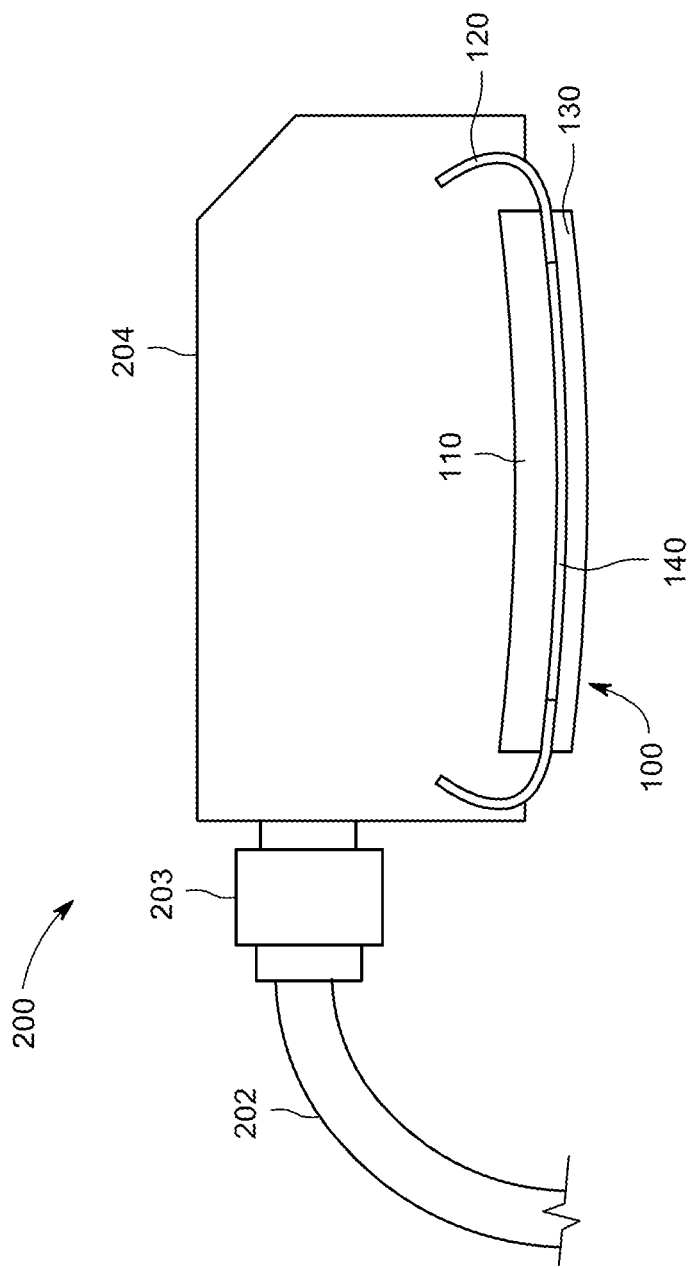
FIG. 5 is a section view of an exemplary ultrasonic inspection system.

FIG. 5 is a section view of an exemplary ultrasonic inspection system 200, which includes the exemplary acoustic stack of the ultrasonic inspection probe assembly 100 (e.g., the face layer 130, the backing block 110, the flexible ultrasonic transducer array frame 120, and the flexible ultrasonic transducer array 140). As shown in FIG. 5, a cable 202 connects to the housing 204 surrounding the ultrasonic inspection probe assembly 100 via a connector 203. The cable 202 can connect the flexible ultrasonic inspection probe assembly 100 to a computing device (not shown). Cable 202 transfers electrical signals between the computing device and the flexible ultrasonic inspection probe assembly 100 to send and receive data and also supply the necessary power to the flexible ultrasonic inspection probe assembly 100. The connector 203 secures the cable 202 to the housing 204. As shown in FIG. 5, the flexible ultrasonic inspection probe assembly 100 can be configured to be in a flexed position in its original state prior to being applied to the test object surface.

To the extent that the claims recite the phrase "at least one of" in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof. "At least one of element A, element B, and element C" is not intended to be limited to at least one of an element A, at least one of an element B, and at least one of an element C.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasonic inspection probe assembly comprising:
a backing block;
a face layer;
a flexible ultrasonic transducer array located between the backing block and the face layer, the flexible ultrasonic transducer array having a top surface and a bottom surface joined by at least one side surface; and
a flexible ultrasonic transducer array frame located between the backing block and the face layer, the flexible transducer array frame comprising a first surface, a second surface opposite the first surface, and an opening extending entirely through a thickness of the flexible ultrasonic transducer array frame from the first surface to the second surface,
wherein the flexible ultrasonic transducer array is positioned within the opening such that the flexible ultrasonic transducer array frame encircles only the at least one side surface of the flexible ultrasonic transducer array, the flexible ultrasonic transducer array frame surrounds each side surface of the flexible ultrasonic transducer array, and the flexible ultrasonic transducer array is coplanar with the flexible ultrasonic transducer array frame.

2. The ultrasonic inspection probe assembly of claim 1, wherein the flexible ultrasonic transducer array and the flexible ultrasonic transducer array frame are bonded the backing block and the face layer with an epoxy to form an acoustic stack.

3. The ultrasonic inspection probe assembly of claim 1, wherein the flexible ultrasonic transducer array is a linear phased array.

4. The ultrasonic inspection probe assembly of claim 1, wherein the flexible ultrasonic transducer array is a matrix phased array.

5. The ultrasonic inspection probe assembly of claim 1, wherein the flexible ultrasonic transducer array is formed from a piezo-ceramic material.

6. The ultrasonic inspection probe assembly of claim 1, wherein the flexible ultrasonic transducer array frame comprises spring steel.

7. The ultrasonic inspection probe assembly of claim 1, wherein a thickness of the flexible ultrasonic transducer array is the same as a thickness of the flexible ultrasonic transducer array frame.

8. The ultrasonic inspection probe assembly of claim 1, wherein the flexible ultrasonic transducer array frame is flexed in an original position when no forces are applied to the ultrasonic inspection probe assembly.

9. The ultrasonic inspection probe assembly of claim 8, wherein the flexible ultrasonic transducer array frame is configured to return to the original position when no forces are applied to the ultrasonic inspection probe assembly.

10. An ultrasonic inspection probe assembly comprising:
a backing block;
a face layer;
a flexible ultrasonic transducer array formed from a piezo-ceramic material and located between the backing block and the face layer, the flexible ultrasonic transducer array having a top surface and a bottom surface joined by at least one side surface; and
a flexible ultrasonic transducer array frame located between the backing block and the face layer, the flexible transducer array frame comprising a first surface, a second surface opposite the first surface, and an opening extending entirely through a thickness of the flexible ultrasonic transducer array frame from the first surface to the second surface,
wherein the flexible ultrasonic transducer array is positioned within the opening such that the flexible ultrasonic transducer array frame surrounds encircles only the at least one side surface of the flexible ultrasonic transducer array, the flexible ultrasonic transducer array frame surrounds each side surface of the flexible ultrasonic transducer array, and the flexible ultrasonic transducer array and the flexible ultrasonic transducer array frame are bonded to the backing block and the face layer with an epoxy to form an acoustic stack.

11. The ultrasonic inspection probe assembly of claim 10, wherein the flexible ultrasonic transducer array is a linear phased array.

12. The ultrasonic inspection probe assembly of claim 10, wherein the flexible ultrasonic transducer array is a matrix phased array.

13. The ultrasonic inspection probe assembly of claim 10, wherein the flexible ultrasonic transducer array frame comprises spring steel.

14. The ultrasonic inspection probe assembly of claim 10, wherein the flexible ultrasonic transducer array frame is flexed in an original position when no forces are applied to the ultrasonic inspection probe assembly.

15. The ultrasonic inspection probe assembly of claim 14, wherein the flexible ultrasonic transducer array frame is configured to return to the original position when no forces are applied to the ultrasonic inspection probe assembly.

16. The ultrasonic inspection probe assembly of claim 1, wherein the flexible ultrasonic transducer array frame is disposed to overlap neither the backing block nor the face layer in a vertical direction when the ultrasonic inspection probe assembly is viewed from the side.

17. The ultrasonic inspection probe assembly of claim 1, wherein a width of the backing block is equal to a width of the face layer, and the respective widths of the backing block and the face layer are greater than a width of the flexible ultrasonic transducer array.

18. The ultrasonic inspection probe assembly of claim 1, wherein the flexible ultrasonic transducer array and the flexible ultrasonic transducer array frame are each formed with a uniform thickness, and the uniform thickness of the flexible ultrasonic transducer array is equal to the uniform thickness of the flexible ultrasonic transducer array frame.

* * * * *